(12) United States Patent
Shin et al.

(10) Patent No.: US 7,250,164 B2
(45) Date of Patent: Jul. 31, 2007

(54) VACCINE COMPOSITION FOR PREVENTING MENINGOCOCCAL DISEASE

(75) Inventors: Jeon-Soo Shin, Seoul (KR); In-Ho Park, Seoul (KR); In-Hong Choi, Seoul (KR); Moon H. Nahm, Birmingham, AL (US)

(73) Assignee: Yonsei University, Seoul (KR)

( * ) Notice: Subject to any disclaimer, the term of this patent is extended or adjusted under 35 U.S.C. 154(b) by 0 days.

(21) Appl. No.: 10/510,720

(22) PCT Filed: Apr. 19, 2003

(86) PCT No.: PCT/KR03/00806

§ 371 (c)(1),
(2), (4) Date: Feb. 3, 2005

(87) PCT Pub. No.: WO03/089473

PCT Pub. Date: Oct. 30, 2003

(65) Prior Publication Data

US 2006/0073139 A1  Apr. 6, 2006

(30) Foreign Application Priority Data

Apr. 19, 2002 (KR) ................. 10-2002-0021462

(51) Int. Cl.
*A61K 39/395* (2006.01)
(52) U.S. Cl. .................. 424/131.1; 530/350
(58) Field of Classification Search .......... 424/131.1
See application file for complete search history.

(56) References Cited

U.S. PATENT DOCUMENTS 6,048,527 A    4/2000  Granoff et al.
6,248,329 B1 *  6/2001  Chandrashekar et al. 424/191.1

OTHER PUBLICATIONS

Greenspan et al. (Nature Biotechnology 17: 936-937, 1999).*
Bowie et al (Science, 1990, 247:1306-1310).*
Ellis (Chapter 29 of Vaccines, Plotkin, et al. (eds) WB Saunders, Philadelphia, 1988, pp. 568-575.*
J. Finne et al., Lancet, Aug. 13, 1983, pp. 355-357.
P.F. Kohler et al., J. Clin. Invest., vol. 75, Mar. 1985, pp. 883-888.
D.W. Pascual et al., Journal of Immunological Methods, vol. 146, 1992, pp. 249-255.
B.D. Livingston et al., The Journal of Biological Chemistry, vol. 263, Jul. 6, 1988, pp. 9443-9448.
E. Rosenstein et al., N. Engl. J. Med., vol. 344, No. 18, May 3, 2001, pp. 1378-1388.
J. Parkhill et al., Nature, vol. 404, Mar. 30, 2000, pp. 502-506.
H. Tettelin et al., Science, vol. 287, Mar. 10, 2000, pp. 1809-1815.

(Continued)

*Primary Examiner*—Robert A. Zeman
*Assistant Examiner*—Brian J. Gangle
(74) *Attorney, Agent, or Firm*—Greenblum & Bernstein, P.L.C.

(57) ABSTRACT

The present invention relates to an anti-idiotype antibodies directed against the monoclonal antibody (HmenB3) to *Neisseria meningitidis* serogroup B and hybridomas producing the anti-idiotype antibodies. This invention is also directed to vaccine compositions comprising the anti-idiotypic antibodies in combination with pharmaceutically acceptable carriers. These vaccine compositions can be used to prevent or treat the serogroup B meningococcal disease.

2 Claims, 12 Drawing Sheets

(A)

(B)

OTHER PUBLICATIONS

D.A.A. Ala Aldeen et al., Journal of Infection, vol. 33, 1996, pp. 153-157.

F.X. Riedo et al., Pediatr. Infec. Dis. J., vol. 14, 1995, pp. 643-657.

J. Finne et al., The Journal of Immunology, vol. 138, No. 12, Jun. 15, 1987, pp. 4402-4407.

J. Nedelec et al., Journal of Neuroimmunology, vol. 29, 1990, pp. 49-56.

H.J. Jennings et al., J. Exp. Med., vol. 165, Apr. 1987, pp. 1207-1211.

D.M. Granoff et al., The Journal of Immunology, vol. 160, 1998, pp. 5028-5036.

R.A. Pon et al., J. Exp. Med., vol. 185, No. 11, Jun. 2, 1997, pp. 1929-1938.

M.A.J. Westerink et al., Proc. Natl. Acad. Sci. USA, vol. 92, Apr. 1995, pp. 4021-4025.

W. Magliani et al., Nat. Med., vol. 4, No. 6, Jun. 1998, pp. 705-709.

J.S. Shin et al., Infection and Immunity, vol. 69, No. 5, May 2001, pp. 3335-3342.

L.J. Harris et al., Biochemistry, vol. 36, 1997, pp. 1581-1597.

J.G. Augustine et al., The Journal of Biological Chemistry, vol. 276, No. 5, Feb. 2, 2001, pp. 3287-3294.

Y. Li et al., Biochemistry, vol. 39, 2000, pp. 6296-6309.

J. Finne et al., Biochemical and Biophysical Research Communications, vol. 112, No. 2, Apr. 29, 1983.

* cited by examiner (A)

Heavy chain
```
Mab231  EVKLQESGGGLVQPGGSLKLSCATSGFTFSDYYMYWVRQTPEKRLEWVAYISNGGGSTYYPDTVKGRFTI
Naid60  ----V-------------------L-T---F-----------------D----------
```
```
        SRDNAKNTLYLQMSRLKSEDTAMYYCARHGG    YYAMDYWGQGT
        ------A---------------------K-YYGY---L-------
```

Light chain
```
MAK33   DIVLTQSPATLSVTPGESVSLSCRASQSISNNLHWYQQKSHESPRLLIKYASQSISGIPSRFSGSGSGTD
Naid60  --Q-----------D---------------------------------------
HyHEL-63 ------------D---------------------------------------
```
```
        FTLSINSVETEDFGMYYCQQSNSWPLTFGAGTK
        ----------------F----N-----------
        ----------------F-------Y---G----
```

Nucleotide and estimated amino acid sequences of Naid60 VH

```
1--------10---------20---------30---------40---------50---------60---------70---------80---------90
GAAGTGAAGTTGGTGGAGTCTGGGGGAGGCTTAGTGCAGCCTGGAGGGTCCCTGAAACTCTCCTGTGCAACCTCTGGATTCGTTTTCACT
 E  V  K  L  V  E  S  G  G  G  L  V  Q  P  G  G  S  L  K  L  S  C  A  T  S  G  F  V  F  T
                                                                         CDR1

GACTATTACATGTTTTGGGTTCGCCAGACTCCAGAGAAGAGGCTGGAGTGGGTCGCATACATTAGTAATGGTGGTGGTGACACCTATTAT
 D  Y  Y  M  F  W  V  R  Q  T  P  E  K  R  L  E  W  V  A  Y  I  S  N  G  G  G  D  T  Y  Y
                                                                      CDR2

CCAGACACTGTAAAGGGCCGATTCACCATCTCCAGAGACAATGCCAAGAACGCCCTGTACCTGCAAATGAGCCGTCTGAAGTCTGAGGAC
 P  D  T  V  K  G  R  F  T  I  S  R  D  N  A  K  N  A  L  Y  L  Q  M  S  R  L  K  S  E  D

ACAGCCATGTATTACTGTGCAAGACATAAGGGCTACTATGGATATTACTATGCTTTGGACTACTGGGGTCAAGGAACC
 T  A  M  Y  Y  C  A  R  H  K  G  Y  Y  G  Y  Y  Y  A  L  D  Y  W  G  Q  G  T
                             CDR3
```

Nucleotide and estimated amino acid sequences of Naid60 VL

```
1--------10---------20---------30---------40---------50---------60---------70---------80---------90
GACATTCAGCTGACCCAGTCTCCAGCCACCCTGTCTGTGACTCCAGGAGATAGCGTCAGTCTTTCCTGCAGGGCCAGCCAAAGTATTAGC
 D  I  Q  L  T  Q  S  P  A  T  L  S  V  T  P  G  D  S  V  S  L  S  C  R  A  S  Q  S  I  S
                                                                         CDR1

AACAACCTACACTGGTATCAACAAAAATCACATGAGTCTCCAAGGCTTCTCATCAAGTATGCTTCCCAGTCCATCTCTGGGATCCCCTCC
 N  N  L  H  W  Y  Q  Q  K  S  H  E  S  P  R  L  L  I  K  Y  A  S  Q  S  I  S  G  I  P  S
                                                             CDR2

AGGTTCAGTGGCAGTGGATCAGGGACAGATTTCACTCTCAGTATCAACAGTGTGGAGACTGAAGATTTTGGAATGTATTTCTGTCAACAG
 R  F  S  G  S  G  S  G  T  D  F  T  L  S  I  N  S  V  E  T  E  D  F  G  M  Y  F  C  Q  Q

AGTAACAACTGGCCTCTCACGTTCGGTGCTGGGACCAAG
 S  N  N  W  P  L  T  F  G  A  G  T  K
         CDR3
```

FIG. 4B

Peptides of Naid60 CDR region

Heavy chain

1. CDR1: CATSGFLFTDYY (12-mer) SEQ ID NO. 10
2. CDR2: VAYISNGGGDTY (12-mer) SEQ ID NO. 11
3. CDR3: CARHKGYYGYYYALD (15-mer:pNaid60) SEQ ID NO. 9

Light chain

1. CDR1: CRASQSISNNLH (12-mer) SEQ ID NO. 12
2. CDR2: LIKYASQSISGIPS (14-mer) SEQ ID NO. 13
3. CDR3: YFCQQSNNWPLTFG (14-mer) SEQ ID NO. 14

(A)

(B)

(A)

(B)

(A)

(B)

(C)

(D)

(A)

(B)

(C)

(A)

(B)

VACCINE COMPOSITION FOR PREVENTING MENINGOCOCCAL DISEASE

TECHNICAL FIELD

The present invention is related to anti-idiotypic antibody to *Neisseria meningitidis* serogroup B (NMGB). Specifically, this invention is related to anti-idiotypic antibody to HmenB3, which is a monoclonal antibody (MAb) against NMGB capsular polysaccharide (PS) and a hybridoma cell line producing this antibody. This invention is further related to the composition containing anti-idiotypic antibody to HmenB3 with pharmaceutically acceptable excipients, for prevention of group B meningococcal disease.

BACKGROUND OF THE INVENTION

Despite the availability of effective antibiotics, bacterial meningitis is still a devastating disease that threatens the lives of children and young adults. The case fatality rate of bacterial meningitis is very high, approximately 20%, with rapid clinical progression upon following infection, and many patients who recover are left with neurological sequelae. Although there are racial and geographical differences, meningitis due to *N. meningitidis* remains a leading cause of bacterial meningitis in the world, which includes the United States and European countries (Rosenstein, N. E., et al., N Engl J Med 344, 1378-1388. (2001)).

The complete genomes of both *N. meningitidis* serogroup A and B has been sequenced respectively (Parkhill, J., et al., Nature 404, 502-506. (2000); and Tettelin H, S. N., et al., Science 287, 1809-1815 (2000)). *N. meningitidis* is one of the most common causes of bacterial meningitis and is divided into 13 serogroups based on chemically and immunologically distinct capsular PSs. Five serogroups, designated A, B, C, Y, and W-135, has been classified as pathogens in humans. However, meningococcal group B strain accounts for approximately 50% of bacterial meningitis (Ala'Aldeen , D. D. A., et al., Journal of Infection 33, 153-157 (1996); Riedo, F. X., et al., Pediatr Infect Dis J 14, 643-657 (1995); and Rosenstein, N. E., et al., N Engl J Med 344, 1378-1388 (2001)). In comparison to other serogroups, serogroup B meningoccal disease is more prevalent in North America and Europe, for unknown reasons. This creates a public health problem in the United States and Europe.

To date, PS-based conjugate vaccines have failed due to the poor immunogenicity of the capsular PS of NMGB. NMGB PS is a homolinear polymer of N-acetyl (2-8) neuraminic acid, and is structurally similar to polysialic acid of neural cell adhesion molecules expressed in human neuronal tissue (Finne, J., et al., Lancet 2, 355-357 (1983)). Thus, NMGB PS has the potential to induce autoantibodies and lead to autoimmune responses (Finne, J., et al., J Immunol 138, 4402-4407 (1987); and Nedelec, J., et al., J Neuroimmunol 29, 49-56 (1990)). Therefore, such problems make it difficult to develop a vaccine against NMGB.

In an attempt to circumvent this problem, Jennings reported an innovative strategy for overcoming the poor immunogenicity to NMGB PS and the cross-reactivity to NCAM, by substitution of N-propionyl for N-acetyl groups of NMGB PS (Jennings, H. J., et al., JEM 165, 1207-1211 (1987)). N-propionyl neuraminic acid polymer is reported to induce antibodies that cause bacteriolysis in vitro, but a subset of antibodies elicited by N-propionyl neuraminic acid have anti-host antibody activity (Granoff, D. M., et al., Journal of Immunology 160, 5028-5036 (1998); and Pon, R. A., et al., J Exp Med 185, 1929-1938 (1997)). This has made a problem in vaccine stability.

Studies using anti-idiotypic antibodies have focused mostly on increasing the immune response to tumor specific antigens, which do not elicit effective immune response due to their poor immunogenicity, and on the production of bacterial vaccine. For example, anti-idiotypic antibody to the capsular PS of *N. meningitidis* serogroup C was prepared and immunization of its anti-idiotypic peptide conjugated with carrier protein could elicit Ab to kill the bacteria (Westerink, M. A. J., et al., Proc Natl Acad Sci USA 92, 4021-4025 (1995)). A further example is that the immunization of mice with bacteriophages containing single chain variable fragment (scFv), which was obtained from anti-idiotypic antibody to *Streptococcus pneumoniae*, showed protective effect against bacterial infection (Magliani, W., et al., Nat Med 4, 705-709 (1998)).

Based on the above references, this inventor developed anti-idiotypic antibody using the properties of HmenB3 in order to provide a vaccine capable of protecting against and treating group B meningococcal disease (Shin, J. S., et al., Infect Immun 69, 3335-3342 (2001)). HmenB3 is a MAb against NMGB PS, which kills NMGB and has no cross-reactivity to NCAM (Shin, J. S., et al., Infect Immun 69, 3335-3342 (2001)).

SUMMARY OF THE INVENTION

This invention is directed to an anti-idiotypic antibody to HmenB3 and active fragments thereof.

Another embodiment of the invention is directed to a hybridoma producing such anti-idiotypic antibody.

Other embodiments of the invention are directed to a vaccine composition comprising the anti-idiotypic antibody and the active fragments in combination with pharmaceutically acceptable excipient, for protection against group B meningococcal disease.

BRIEF DESCRIPTION OF THE FIGURES

FIG. 4A depicts the nucleotide sequences and the deduced amino acid sequences of the variable regions of Naid60's heavy chains (SEQ ID NOS: 7 and 5, for the nucleotide and amino acid sequences, respectively) and light chains (SEQ ID NOS: 8 and 6, for the nucleotide and amino acid sequences, respectively). The CDR regions of VH and VL of Naid60 were deduced (underlined) by comparison with the known crystal structures of VH and VL with the closest nucleotide sequences of Mab231 (SEQ ID NO: 15), MAK33

(SEQ ID NO: 16), and HyHEL-63 (SEQ ID NO: 17). FIG. 4B depicts the deduced peptide sequences of CDR1 (SEQ ID NO: 10), CDR2 (SEQ ID NO: 11), CDR3 (SEQ ID NO: 9) of the heavy chains of Naid60 and of CDR1 (SEQ ID NO: 12), CDR2 (SEQ ID NO: 13), CDR3 (SEQ ID NO: 14) of the light chains of Naid60. The peptide of heavy chain CDR3 was named pNaid60.

BRIEF DESCRIPTION OF SEQUENCES

Figure 1:
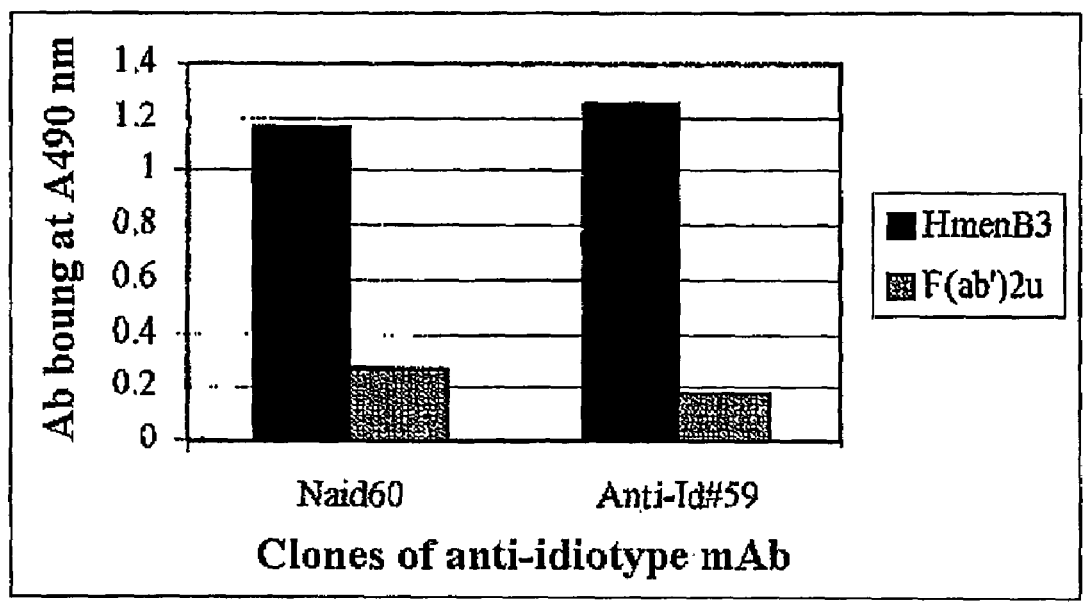
FIG. 1 depicts the inhibition of binding of HmenB3 to NMGB-coated microplate by one of representative anti-idiotypic MAbs that bind to HmenB3. (A) shows that two representative anti-idiotypic MAbs (Naid60 and Anti-Id#59) bind to HmenB3 and (B) shows that only Naid60 (IgG1, kappa light chain) inhibits the binding of HmenB3 to NMGB.
Figure 1:
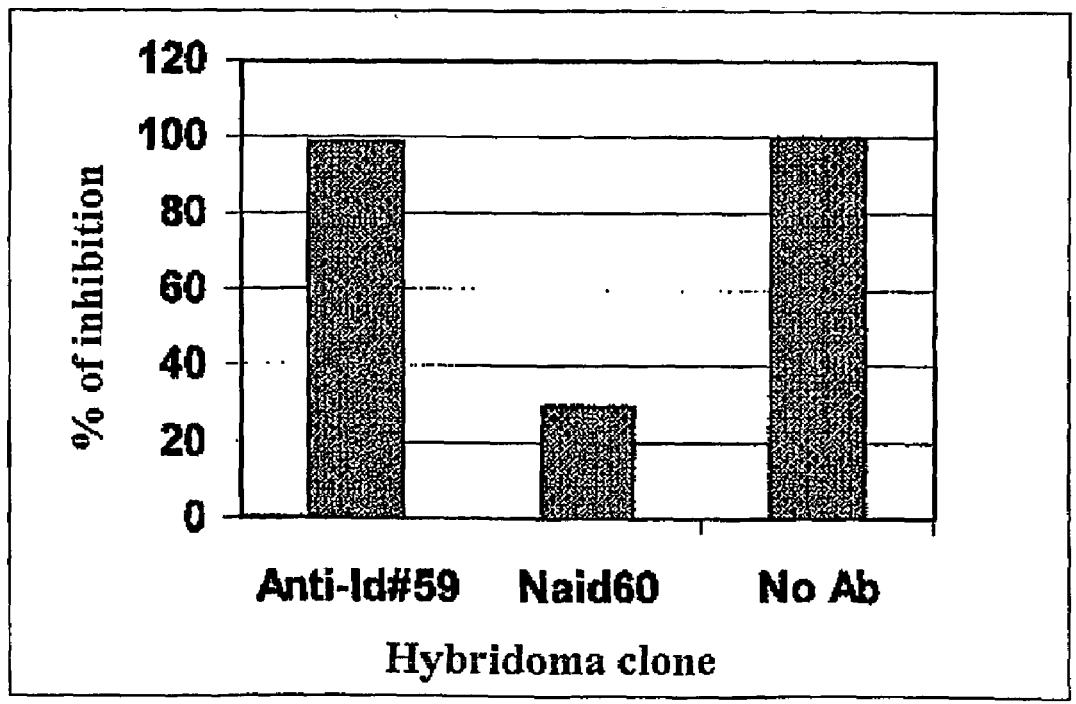

SEQ ID. NOs: 1 and 2 are the sense and anti-sense primers used for amplification of the variable region of H chain of Naid60, respectively.

SEQ ID. NOs: 3 and 4 are the sense and anti-sense primers used for amplification of the variable region of L chain of Naid60 antibody, respectively.

SEQ ID. NOs: 5 and 6 are the deduced amino acid sequences from the nucleotide sequences of the variable regions of H and L chain of Naid60, respectively.

SEQ ID. NOs: 7 and 8 are the nucleotide sequences of the variable regions of H and L chain of Naid60 antibody, respectively.

DETAILED DESCRIPTION OF THE INVENTION

In describing the present invention, many terms will be employed and are intended to be interpreted as indicated below.

As used herein, Ab1 refers to an antibody binding to a specific antigen or infectious agent and containing idiotype directly involved in antigen binding. In case of the present invention, Ab1 refers to HmenB3 which specifically binds NMGB PS but does not cross-react with NCAM. Immunization with Ab1 idiotype produces Ab2 anti-idiotype, which contains an "internal image".

As used herein, Ab2 anti-idiotype mimics the three dimensional structure of an antigen, so the anti-idiotype and antigen bind to the same site on the Ab1-binding region. Immunization with anti-idiotypic Ab (Ab2) elicits anti-anti-idiotypic antibody (termed as Ab3 or Ab1'). The specificity of Ab3 (Ab1') is equivalent to Ab1. Such antigenic mimicry property of the anti-idiotypic antibody can be useful as an alternative antigen (or idiotype vaccine) when an immunogen is difficult to use or prepare.

As used herein, the anti-idiotypic antibody (Ab2) that binds to Ab1 (HmenB3) is named Naid60. Thus, Naid60 has an epitope which structurally mimics NMGB PS.

As used herein, Ab3 (Ab1')refers to anti-Naid60 antibody, 2-7-34. This antibody has bactericidal activity against NMGB, like Ab1 (HmenB3), in the presence of rabbit complement, and shows no autoimmune response.

Antibody fragment, as used herein, encompasses $F(ab')_2$, Fab', and Fab. Regardless of their structures, these antibody fragments can bind to the same antigen as that recognized by the whole antibody. Active fragment of Naid60 recognizes the idiotype of HmenB3 and mimics the epitope of NMGB PS.

As used herein, antibody fragment also encompasses the synthetic peptide or recombinant antibody from Naid60 that exhibits immunologically binding properties. Further specifically, antigen fragment encompasses the fragment of the variable regions of heavy and light chain, Fv fragment. Single chain variable fragment (scFv) is composed of Fv fragments of the VH and VL, which are linked with a peptide linker.

As used herein, humanized antibody, for example, refers to recombinant antibody protein that the CDRs of H and L chain of mouse antibody are saved and the other regions of Ab replaced with human variable region.

Generally, antibody fragment can be obtained from digestion of whole antibody with pepsin (or papain) by a common method. For example, $F(ab')_2$ fragment can be obtained from pepsin digestion of antibody. Fab' can also be obtained by addition of thiol reducing agent to $F(ab')_2$.

As used herein, Fv fragment is the fragment from the binding region of the VH and VL. Such binding can be covalent or non-covalent but a covalent bond with a peptide linker is desirable. Such scFv can be obtained from a structural gene constructed by linking DNA sequences encoding variable regions of H and L chain. When the structural genes of VH and VL with a linker are introduced into an expression vector and transformed into a host cell, for example, E. coli, scFv can be obtained as a single polypeptide chain.

As used herein, hybridoma technology is a well-known skill in the art (Kohler, P. F., et al., J Clin Invest 75, 883-888 (1985)). Hybridoma refers to the cell produced by fusion of an antibody producing cell and an immortalized cell, such as a myeloma cell. This hybridoma can produce antibody continuously. Typically, splenocytes from mouse immunized with a specific antigen are fused to an immortalized cell line (typically myeloma cells). The culture supernatants of hybridoma cells can be screened for selection of specific antibody to a target antigen.

As used herein, an antibody directed to NMGB PS or hybridoma producing this antibody can be used as an immunogen to produce anti-idiotypic monoclonal antibody. In this invention, HmenB3 is used as the immunogen (Ab1) that elicits anti-idiotype monoclonal antibody, Naid60 (Ab2). To obtain HmenB3, hybridoma cells producing HmenB3 antibody were ip inoculated into pristine-pretreated mice. HmenB3 was obtained from mouse ascites and purified through size-exclusion column chromatography with Sephacryl S-300HR.

Immunization can be performed by standard methods well known in the art. Dosage and regimen required for immunization vary according to species, the immune condition, and the weight of animals which are immunized. Generally, antisera from immunized animal can be obtained and analyzed for specific antibodies using proper screening assays.

Typically, an immortalized cell line (such as myeloma cell) is derived from the same species of animal as provided the lymphocytes. Preferable immortalized cell line is murine myeloma cell sensitive to culture media containing hypoxanthine, aminopterin, and thymidine ("HAT medium"). HAT-sensitive murine myeloma can be fused to mouse splenocytes with polyethylene glycol. After fusion, hybridoma cells can be selected by HAT medium which kill unproductively fused myeloma cells (in case of splenocytes not fused, they will be killed in several days). Hybridomas producing desirable antibodies can be selected by screening the culture supernatants of hybridomas.

To prepare the hybridoma producing antibody as used herein, mouse spleen was removed and dissociated into single cells from mouse immunized with $F(ab')_2$ fragment of HmenB3. These splenocyes were mixed with murine myeloma cells, P3-X63-Ag8.653 and fused with polyethylene glycol. Hybridomas were selectively cultured in HAT medium, and contiuously maintained in HT medium. As a result, a hybridoma producing Naid60 was obtained. This hybridoma was deposited with deposit number "KCTC10228BP" in Korean Collection for Type Cultures of Korea Research Institute of Bioscience and Biotechnology.

In order to produce anti-idiotypic antibody as used herein, hybridoma cells were fully cultured in conditional enriched medium to secrete monoclonal antibody into the medium. Media for hybridoma culture are well known in the art. Culture supernatant can be collected and purified by a general method well known in the art. Desirable antibody can be produced in mice pretreated with 2,6,10,14-tetramethylpentadecane (Pristane) and inoculated ip with hybridoma cells. Normally, hybridoma produces antibody, and high concentrations of antibody can be obtained from the ascites of mice.

Recombinant antibody as used herein can be produced by general recombinant technology, for example, a technique in which an expression vector containing DNA encoding H chain and L chain of a desirable antibody can be transformed into host cells. In addition, the part of H chain or hinge and constant region and/or constant region of L chain of antibody as used herein can be modified into a recombinant chimeric antibody by replacing the corresponding region of H or L chain of immunoglobulin with those of other species, and it is possible to produce recombinant humanized antibody by grafting CDRs of antibody to corresponding CDRs of human antibody in order to reduce the antigenicity of the antibody.

As used herein, anti-idiotypic antibody directed to HmenB3 or its active fragment (such as scFv or $F(ab')_2$) can be administered to patients in order to induce the specific immune response to NMGB. Such immune response can be useful for protection of patients at risk of exposure to NMGB.

Naid60 and its active fragment as used herein can be conjugated to soluble immunogenic carrier protein used for vaccine composition. Keyhole limpet hemocyanin (KLH) and toxoid are available protein carriers for vaccine. Antibody and its active fragments can be conjugated to carrier protein by methods well known in the art. Desirable vaccine compositions can comprise antibody-carrier protein conjugates or antibody fragment-carrier protein with adjuvant. Suitable adjuvant contains aluminum hydroxide and lipid. The formulation of vaccine compositions can be prepared by a method well known in the art.

In addition, pharmaceutical compositions can be formulated by mixing antibody or antibody fragment with pharmaceutically acceptable excipient by a method well known in the art. In case a composition has been appropriately evaluated for safety in an animal model, this composition refers to pharmaceutically acceptable excipient in a drug delivery system. Phosphate-buffered saline is one of the examples, and many suitable excipients are well known in the art. Generally, antibody as used herein can be suspended in sterilized saline. Pharmaceutical compositions can be formulated selectively to control release of the active composition or to extend the release of compositions in systemic circulation. Various suitable drug delivery systems are well known in the art. For example, there are grafting drug delivery system, Hydrogel, Hydroxymethylcellulose, microcapsule, liposome, microemulsion, microsphere etc. Delivery of pharmaceutical compositions as used herein can include oral administration, or non-oral such as intranasal, intrasubcutaneous, intramuscular, intravenous, and intraarterial administration etc. But intravenous and non-oral administration is conventionally desirable.

Below are examples of specific embodiments for carrying out the present invention. The examples are offered for illustrative purposes only, and are not intended to limit the scope of the present invention in any way.

EXAMPLE

Bacteria

All *Neisseria* strains (ATCC 13090 and H44/76) were grown on chocolate agar plates in a candle jar. To obtain a large number of *Neisseria* bacteria with minimal biohazard, all chocolate agar plates were plated with the bacteria and the bacteria were then harvested from the plates after 6-h incubation at 37° C. All bacteria were aliquoted in Hanks' balanced salt solution (HBSS) containing 20% glycerol and stored at −70° C.

Example 1

Preparation of $F(ab')_2$ Fragment of HmenB3 and Immunization

Ascites was obtained from pristine-pretreated mouse injected ip with hybridoma cells producing HmenB3 (IgM, kappa light chain). HmenB3 was purified from the ascitic fluid of mice by size-exclusion column chromatography using Sephacryl S-300HR (Pharmacia, Uppsala, Sweden), and $F(ab')_2$ fragments were purified after pepsin proteolysis at 4° C. (Pascual, D. W., et al., J Immunol Methods 146, 249-255 (1992)). Two mg of F(ab')$_2$ fragments were added in the same amount of KLH, and mixed slowly with the same volume of 2% glutaraldehyde solution for 15 min and then incubated for 30 min. The remaining glutaraldehyde was blocked by addition of glycine up to 200 mM final concentration. After dialysis with PBS solution, F(ab')$_2$-KLH conjugate was prepared. BALB/c mice were immunized ip with 100 µg of F(ab')$_2$-KLH conjugate with complete Freund's adjuvant. Booster immunizations were performed on a biweekly basis with Freund's incomplete adjuvant. Three days prior to fusion, the mice were boosted intravenously through tail-vein with 100 µg of F(ab')$_2$ and splenectomized for fusion.

Example 2

Production and Analysis of Monoclonal Antibody

After mouse spleen was dissociated into single cells, the splenocytes were fused with P3-X63-Ag8.653 myeloma cells by polyethylene glycol method. Hybridoma cells were selectively cultured in HAT medium and maintained in HT medium. Antibody bound to HmenB3 or F(ab')$_2$ fragment of HmenB3 by ELISA was selected, and isotyping was performed using the mouse-hybridoma subtyping kit (Boehringer Mannheim GmbH, Germany).

Example 3

Enzyme-linked Immunosorbent Assay (ELISA)

ELISA was used for screening monoclonal antibodies. Briefly, EIA plates (Corning Inc., Corning, N.Y.) were added with 100 µl of 10 µg/mL antigen diluted in carbonate-bicarbonate buffer, pH 9.6 and incubated overnight at 4° C. The plates were then washed with 0.05% (v/v) Tween 20 (polyoxyethylene sorbitan monolaurate) in phosphate-buffered saline (PBST, pH 7.4) and blocked with 5% (v/v) normal goat serum in PBST (NGS-PBST) for 1 hr. After that, 100 µl of hybridoma culture supernatant was added to each well and incubated for 90 min at 37° C. After washing 4 times with PBST, horseradish peroxidase (HRP)-labeled goat anti-mouse immunoglobulin G (Sigma) was added and incubated in each well. After 90 min. incubation, plates were washed 4 times with PBST and O-phenylenediamine (OPD) solution was added to the plates. Optical densities of the plates were measured at 490 nm.

To test the specificity of anti-idiotypic MAb (named Naid60) to HmenB3, inhibition ELISA assay was performed. Briefly, EIA microplates were coated with NMGB (ATCC No. 13090) by adding and drying up 100 µl of PBS containing heat-killed NMGB (optical density at 620 nm=0.09) to each well. Purified *E. coli* K1 PS was used as a coating antigen as well. After washing and blocking the plates, HmenB3 was added to each well in the presence of various concentrations of anti-idiotypic MAb and then the plates were incubated for 3 hr at room temperature with agitation. HRP-labeled goat anti-mouse immunoglobulin and OPD solution were used as a secondary antibody and a substrate, respectively.

Example 4

Bactericidal Assay

The bactericidal assay was performed in 96-well microtiter plates (Corning Inc., Corning, N.Y.). Briefly, 30 µl of bacterial suspension containing 2,500 CFU, 50 µl of appropriately diluted antibiotic-free antibody, and 20 µl of baby rabbit complement were added to each well. To measure the bactericidal inhibition by Naid60, 25 µl of appropriately diluted antibiotic-free antibody and 25 µl of Naid60 were added together instead of 50 µl of appropriately diluted antibiotic-free antibody. After a 1-h incubation with shaking, 10 µl of the reaction mixture was plated on a chocolate agar plate (Shin, J. S., et al., Infect Immun 69, 3335-3342 (2001)). CFU was determined after an overnight incubation at 37° C. in a candle jar. An isotype-matched irrelevant monoclonal antibody was used as a negative control. Each assay was performed in triplicate, and the mean of the triplicate was used to calculate the percentage of killing by the formula [(CFU$_{no\ antibody}$−CFU$_{sample}$)/CFU$_{no\ antibody}$]×100.

Example 5

Sequence Analysis of Variable Region of Naid60

Total RNA was prepared from hybridoma cultured in RPMI1640 containing 10% fetal bovine serum by using RNeasy Miniprep kit (Qiagen, GmbH, Germany). cDNA was synthesized using MMLV reverse transcriptase and RT-PCR was performed for amplification of VH and VL. PCR conditions were as follows: 1.5 mM MgCl$_2$, 0.2 mM dNTP, 2.5 U of Taq polymerase (Takara, Japan), denaturation at 95° C. for 1 min, annealing at 55° C. for 1 min, and extension at 72° C. for 1 min. Total number of cycles was 35, and final extension was performed at 72° C. for 10 min. The H chain primers were used as follows: 5-CAGCT-TGATTTTCCTTGTCCTTAT-3 (sense, named as SEQ ID. NO: 1) and 5-GTGCACACCGCTGGACAGGGATCC-3 (anti-sense, named as SEQ ID. NO: 2). The L chain primers were used as follows: 5-GACATTCAGCTGAC-CCAGTCTCCA-3 (sense, named as SEQ ID. NO: 3) and 5-TGGTGGGAAGATGG-3 (anti-sense, named as SEQ ID. NO: 4).

PCR DNA products were purified using PCR purification kit (QUIAGEN), and then sequenced using the dideoxy termination reaction method with Big Dye Terminator Cycle sequencing kit (Applied Biosystems, Foster city, Calif.). Nucleotide sequence was analyzed using a DNA sequencer (Applied Biosystems). The CDRs of VH and VL were analyzed by the V-Quest program. The DNA sequences of variable regions of Naid60 are shown in SEQ ID NO:7 and SEQ ID NO:8.

Example 6

Synthesis of Peptide

The CDR regions of the variable regions of H and L chain of Naid60 were deduced for the identification of anti-idiotype region. the VH and VL of Naid60 were compared for homology to monoclonal antibodies by the BLAST tool at NCBI, and the CDR regions of Naid60 were estimated from the known crystal structure of these antibodies. The peptide of pNaid60 (CARHKGYYGYYYALD) (SEQ ID NO:9) was synthesized for the test of binding to HmenB3. The deduced CDR3 of VH is underlined and CARH was made at the N-terminal flanking regions of CDR3 for the purpose of conjugation or labeling.

pNaid60 was conjugated to BSA (pNaid60-BSA) and tested for binding to HmenB3. Binding to HmenB3 was determined on an EIA microplate coated with the various concentrations of pNaid60-BSA. In addition, competitive ELISA was performed on EIA microplates coated with *E. coli* K1 PS in order to test whether pNaid-BSA can inhibit the binding of HmenB3 to *E. coli* K1 PS. Unconjugated BSA was used for a negative control.

Example 7

Mouse Immunization

Mouse immunizations were performed using two preparations of Naid60. Naid60 or pNaid60 was conjugated to KLH and a total of 100 μg of Naid60-KLH or pNaid60-KLH per mouse was ip injected to three BALB/c mice after emulification with complete Freund's adjuvant. Booster injections were administered four times on a biweekly basis with incomplete Freund's adjuvant. KLH alone was used as negative control. Serum samples were collected 7 days after each injection and stored at −20° C., and the activity of antibody binding was measured to the wells coated with NMGB by ELISA. For ELISA, inactivated NMGB was used as antigen, and the binding with NMGB was measured with diluting mouse serum Example 8

Preparation of Phage Containing Single Chain Variable Fragment (scFv) and Protein Synthesis We produced recombinant Ab of scFv using Naid60 to confirm that Naid60 is an anti-idiotype MAb to HmenB3 and to use it as an immunogen. A scFv phage display library was prepared with the mouse scFv module/recombinant phage display system according to the manufacturer's instructions (Amersham Pharmacia Biotech, Piscataway, N.J.). Briefly, total RNA was isolated from Naid60 hybridoma cells and cDNA was prepared using MMLV reverse transcriptase. cDNA was used in the amplification of the variable regions of heavy and light chains. Thereafter, VH and VL were assembled by utilization of a linker sequence. The product was digested with StfiI and NotI (New England Biolabs) and ligated into pCANTAB5E vector (Amersham Pharmacia Biotech). The ligation mixture was transformed into *E. coli* TG1 cells and the phages were rescued by the helper phage M13KO7. The phage stock was prepared and phage selection was performed by one round of panning on the plate coated with HmenB3.

The phage giving a positive ELISA signal on HmenB3-coated wells was used to produce soluble scFv antibodies. For the production of soluble scFv antibodies, the pCAN-TEB containing scFv gene was digested with Sfi I and Not I and scFv DNA was ligated into the pRSET Sfi I/Not I expression vector. Upon co-expression of the ligation mixture into *E. coli* BL21(DE3), affinity-purified Naid-scFv antibodies were collected. Western blot analysis of purified Naid60-scFv antibody showed a single monomer band with the expected molecular weight of 30 kDa. In addition, ELISA analysis was performed for the inhibition of binding of HmenB3 to EIA microplate coated with NMGB or Naid60 in the presence of various concentrations of scFv Ab of Naid60 as described in <EXAMPLE 3>. A Bactericidal assay was performed in order to test whether recombinant scFv inhibits the bactericidal activity of HmenB3 to NMGB as described in <EXAMPLE 4>.

Example 9

Production of Anti-Naid60 Monoclonal Antibody

Figure 2:
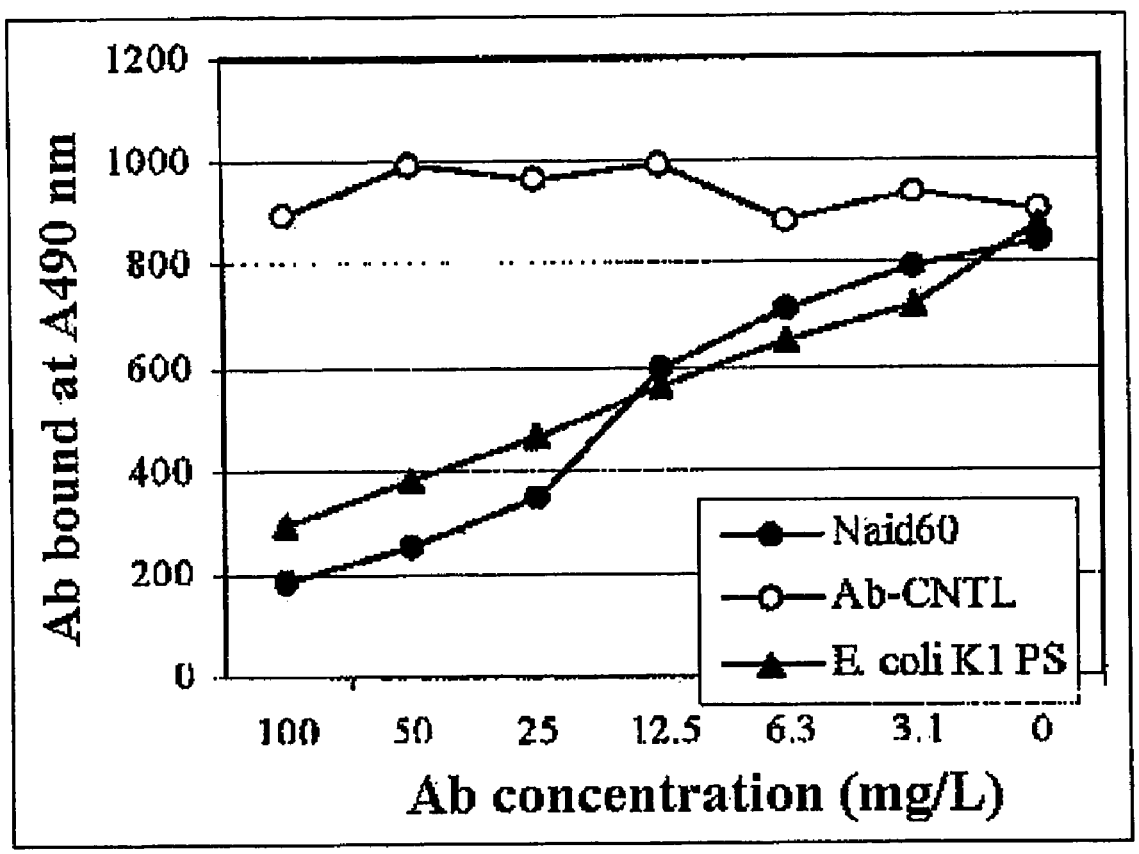
FIG. 2 depicts the inhibition of binding of HmenB3 to NMGB by various concentrations of Naid60. The result shows that the binding of HmenB3 to NMGB was gradually inhibited by increasing concentrations of Naid60. *E. coli* K1 PS is structurally identical with NMGB PS and was used as a positive control.

To further evaluate whether Naid60 mimics NMGB PS to elicit Abs that kill NMGB, we produced anti-anti-idiotypic MAb (Ab3) by immunizing mice with F(ab')2 of Naid60, which was conjugated with KLH. Briefly, Naid60 (IgG1, kappa light chain) was purified from the ascitic fluid of mice by protein G affinity column (Sigma) and $F(ab')_2$ fragments were purified after pepsin proteolysis at 4° C. $F(ab')_2$ fragments were conjugated with KLH as described in <Example 1>, and 100 μg of conjugate was emulsified with complete Freund's adjuvant and ip injected into mice. Mice were boosted on a biweekly basis with incomplete Freund's adjuvant. Three days prior to fusion, primed mice were boosted intravenously through the tail vein with 100 μg of Naid60 and splenectomized for fusion as described in <EXAMPLE 2>. Hybridomas specific to Naid60 were screened using microtiter plates coated with Naid60. One hybridoma clone (named as 2-7-34) that bound to Naid60 was produced. The bactericidal assay and bactericidal inhibition assay to NMGB were performed as described in <EXAMPLE 4>.

Example 10

Binding of 2-7-34 MAb to the Neuronal Cell Adhesion Molecules

To test MAb for binding to the polysialic acid portion of NCAM, CHP-134 cells (Livingston, B. D., et al., J Biol Chem 263, 9443-9448 (1988)) were stained with MAb for flow cytometry as described below. CHP-134 is a human neuroblastoma cell line expressing polysialic acid on the surface of its membrane. Anti-CD56 (Phar Mingen, San Diego, Calif.), which is specific for NCAM, and HmenB1 were used for the positive controls (Shin J S., et al., Infect Immun 69(5): 3335-3342 (2001)), and isotype-matched irrelevant mouse MAb was used as a negative control. In addition, immunohistochemical stainings were performed with the brains obtained from 1- to 2-week-old C57BL/6 mice. Five-micrometer-thick cryosections of the brain were incubated with various concentrations of MAbs for 75 min at RT. The slides were incubated with biotin-conjugated goat anti-mouse Ig (Dako, Glostrup, Denmark) and then with streptavidin-peroxidase after washing. The slide was developed with a peroxidase substrate, 3-amino-9-ethylcarbazole and counterstained with Mayer's hematoxylin stain.

EXPERIMENTAL EXAMPLE

Example 1

Characterization of Anti-idiotype Monoclonal Antibody of Naid60

From five mice immunized with F(ab')2 of HmenB3, we obtained hybridomas producing monoclonal antibody binding to HmenB3. To test the binding specificity of Naid60 to the idiotype of HmenB3, we examined the inhibition of binding of HmenB3 to the wells coated with NMGB in the presence of purified Naid60. Among two monoclonal antibodies which bind to HmenB3 (FIG. 1A), Naid60 could inhibit the binding of HmenB3 to NMGB-coated microtiter plate (FIG. 1B). Naid60 caused dose-dependent inhibition of binding of HmenB3 to NMGB when tested in a competitive ELISA and showed the similar inhibition pattern as like the purified *E. coli* K1 PS (FIG. 2). These data suggest that Naid60 is an anti-idiotypic monoclonal antibody to HmenB3.

Example 2

Bactericidal Inhibition Assay

Figure 3:
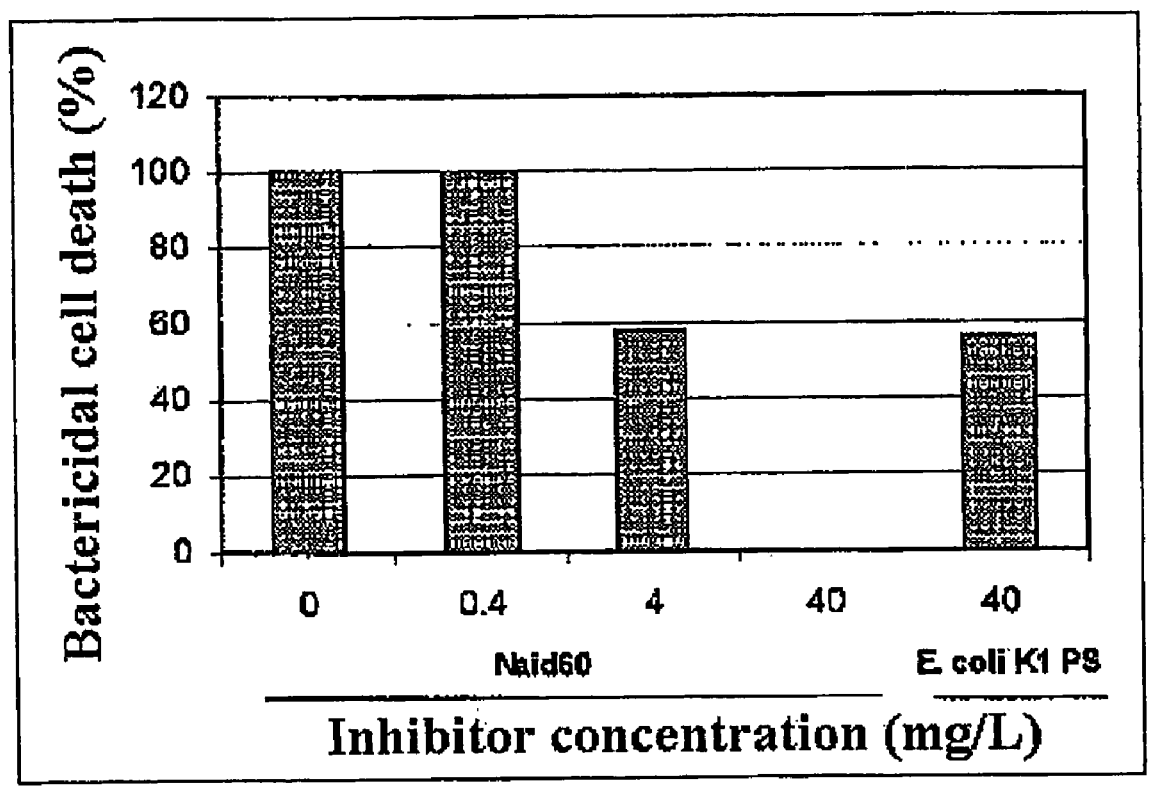
FIG. 3 depicts the inhibition of bactericidal activity of HmenB3 to NMGB strain ATCC No. 13090 by Naid60. The result shows the bactericidal activity of HmenB3 to NMGB was decreased by the addition of Naid60. *E. coli* K1 PS was used for the positive control.

To test whether Naid60 binds the antigen binding sites of HmenB3 and inhibits the ability of HmenB3 to NMGB, the bactericidal inhibition assay was performed in the presence of Naid60. As shown FIG. 3, Naid60 inhibited the killing ability of HmenB3 to NMGB in the presence of rabbit complement in a dose-dependent manner. The bacterial cell death rate was 57.7% and 0% at Naid60 concentrations of 4 mg/L and 40 mg/L respectively when the bactericidal activity of HmenB3 was tested in the presence of Naid60. The killing rate of HmenB3 to bacterial cells was 56.2% when 40mg/L of *E. coli* K1 PS was used as a positive control inhibitor (FIG. 3). These results show that Naid60 binds to the antigenic binding site of HmenB3 and inhibit the bactericidal activity of HmenB3.

Example 3

DNA Analysis of the Variable Region of Naid60

Total RNA was prepared from Naid60, cDNA was produced by reverse transcription and used for amplification of VH and VL of Naid60. DNA sequences of VH and VL were analyzed in both directions using direct DNA sequencing of the PCR products and amino acid sequences were deduced (FIG. 4B). The CDRs of VH and VL of Naid60 were compared to the known crystal structures of VH and VL of other related monoclonal antibodies, which have the closest nucleotide sequences (FIG. 4A). The VH of canine lymphoma monoclonal antibody, Mab231, has the greatest amino acid sequence homology to that of Naid60 (Harries L J, et al., Biochemistry 36:1581-97, (1997)). And the VL of MAK33 (Augustine, J. G., et al., J Biol Chem 276, 3287-3294 (2001)) and of HyHEL-63 (Li, Y., et al., Biochemistry 39, 6296-6309 (2000)) have the greatest amino acid sequence homology to that of Naid60 (FIG. 4).

Example 4

Preparation of Antibody Fragment of Naid60 and Measurement of Antigenicity

Figure 5:
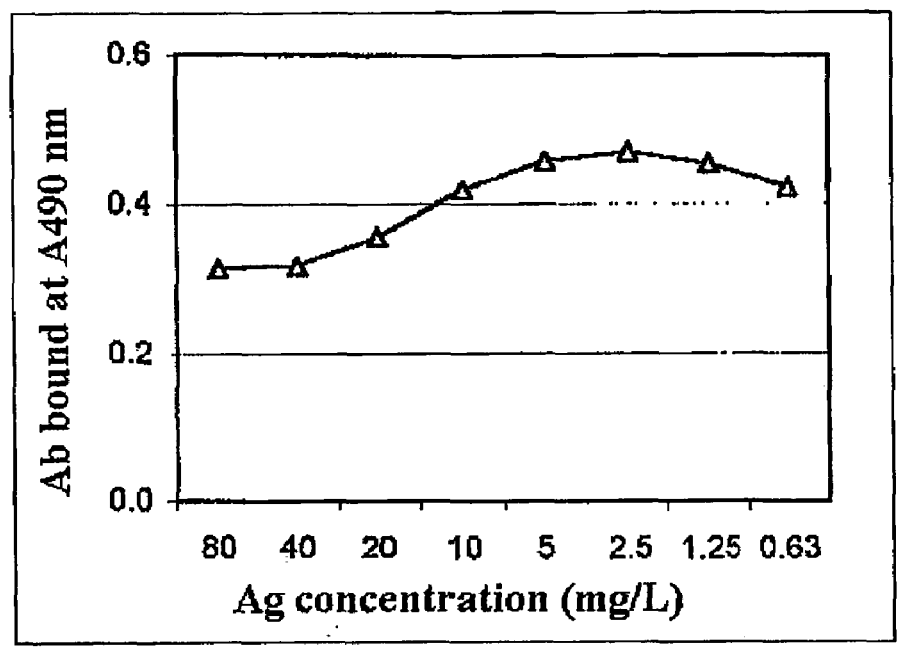
FIG. 5 depicts the binding of synthetic pNaid60 (CDR3 peptide of heavy chain of Naid60) to HmenB3. (A) pNaid60 was synthesized and conjugated with bovine serum albumin (pNaid60-BSA). Varying amounts of pNaid60-BSA were coated to the wells and the binding of HmenB3 to the wells was measured. The results show that the binding of HmenB3 depends on the amount of pNaid60-BSA. (B) The binding of HmenB3 to the wells coated with E. coli K1 PS was inhibited in the presence of pNaid60-BSA.
Figure 5:
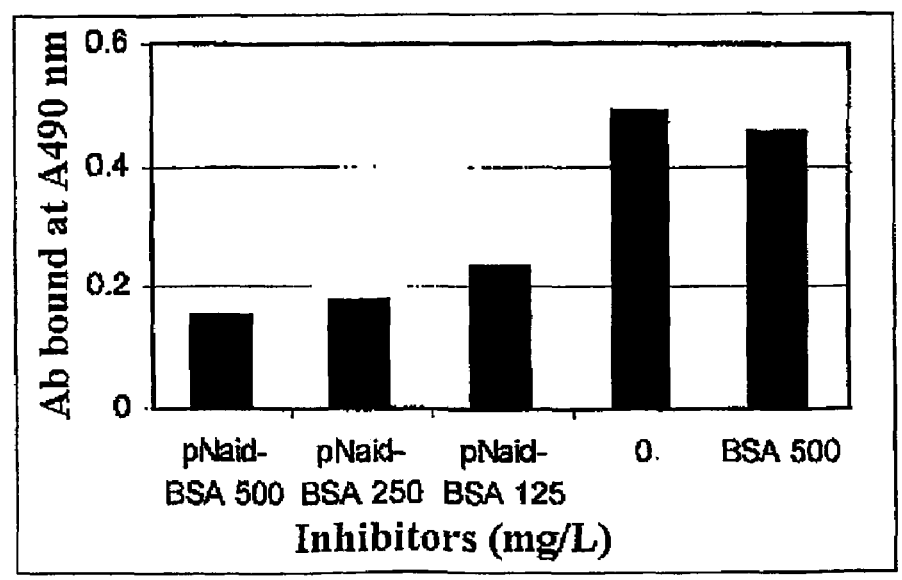

It is important that Naid60 (Ab2) elicits Ab to bind and kill NMGB for the development of anti-idiotype antibody vaccine to NMGB. Thus, it was hypothesized that the heavy chain CDR3 of Naid60 plays a critical role in binding to HmenB3. To examine the binding of HmenB3 to CDR3 of Naid60 VH, pNaid60 was synthesized and conjugated to BSA. pNaid60 is a 15-mer peptide of CARHKGYYGYYY-ALD (SEQ ID NO: 9), which includes the CDR3 of Naid60 VH. ELISA was performed on a microplate coated with pNaid60-BSA to observe the binding of HmenB3 to pNaid60-BSA. The binding of HmenB3 to pNaid60-BSA increased according to increasing pNaid60 concentrations to 2.5 mg/L, and then decreased at higher concentrations, by the antigen excess phenomenon (FIG. 5A).

In order to confirm the specific binding of HmenB3 to pNaid60, competitive ELISA was performed. When we examined the binding inhibition of HmenB3 to microwells coated with *E. coli* K1 PS by pNaid60-BSA, the binding of HmenB3 to *E. coli* K1 PS was reduced 53% and 64% by the addition of pNaid60-BSA to final concentrations of 125 mg/L and 250 mg/L respectively. On the contrary, the unconjugated BSA had little effect on the binding of HmenB3 to *E. coli* K1 PS. Thus, these data suggest that pNaid60 may be one of anti-idiotopes of Naid60.

Figure 6:
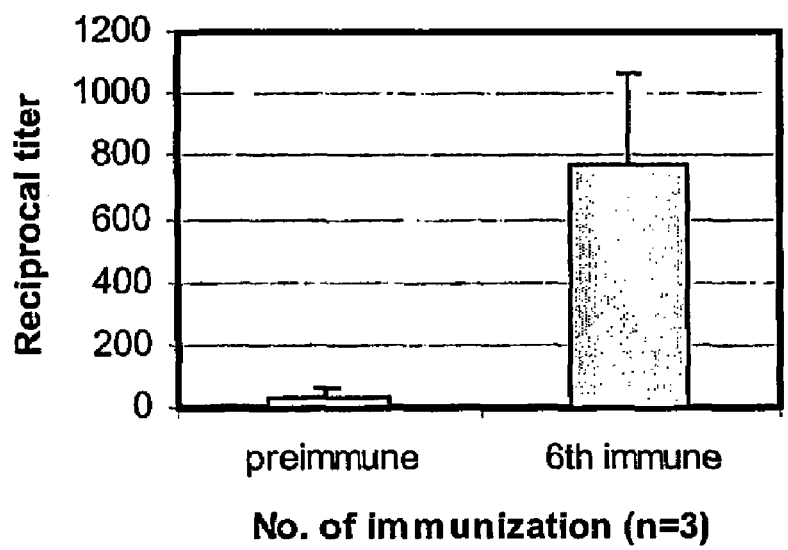
FIG. 6 depicts the production of Ab to NMGB before and after immunization with Naid60. $F(ab')_2$ fragment of Naid60 (A) and recombinant Ab of scFv of Naid60 (B) were emulsified with complete Freund's adjuvant and ip injected into BALB/c mice. Those mice were boosted at 2-week intervals with incomplete Freund's adjuvant and immune sera were collected 7 days after each immunization. The activity of antibody binding to NMGB coated wells was measured by ELISA.
Figure 6:
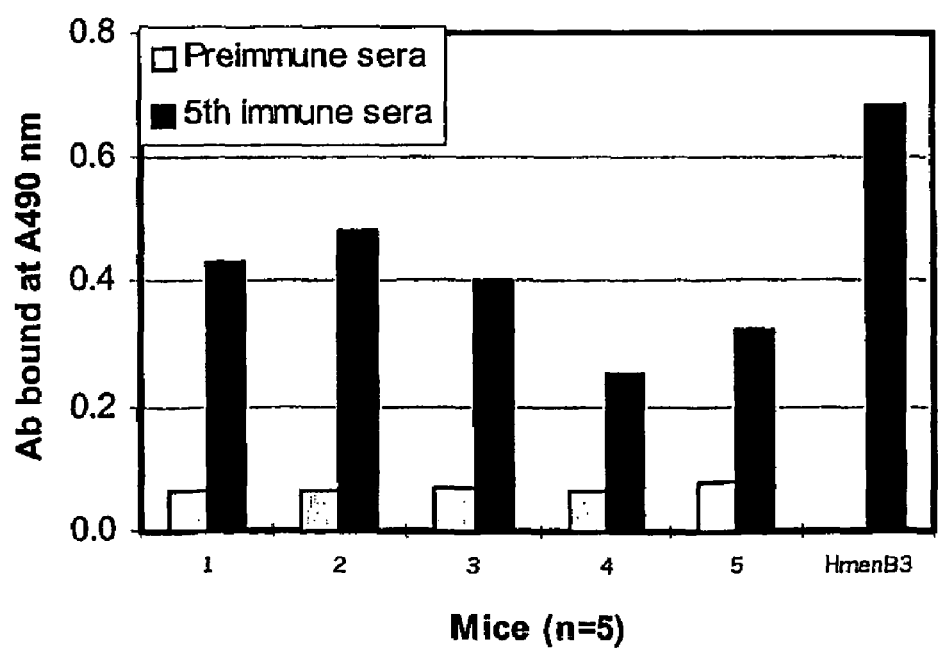

From mice immunized with Naid60-KLH (or BSA) and pNaid60-KLH (or BSA), immune sera were obtained and the antibody titers to NMGB were measured. The Ab titers to NMGB increased with the injection times of Naid60-KLH (or BSA) and pNaid60-KLH (or BSA) (data not shown). $F(ab')_2$ and scFv fragments of Naid60 elicited antibodies to NMGB, as described above. $F(ab')_2$ of anti-idiotypic antibody as used herein could be obtained by a method well known in the art. As described above, scFv is a recombinant antibody fragment expressed in host cells transformed with an expression vector containing DNA encoding the variable region of heavy and light chains. From mice immunized with scFv and F(ab')2, immune sera containing the antibody titers to NMGB could be obtained (FIGS. 6A and 6B).

Thus, these data suggest that Naid60 has the peptide mimicry site to NMGB PS to elicit antibody.

Example 5

Characterization of Single Chain Variable Fragment of Naid60

Figure 7A:
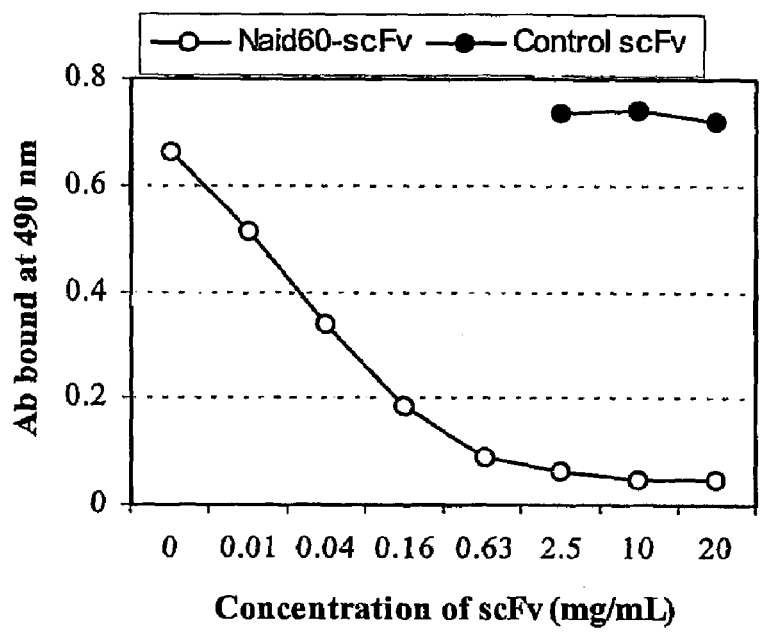
FIG. 7 depicts the antibody reactivity of scFv fragment of Naid60 antibody. scFv fragment of Naid60 inhibited the binding of HmenB3 to the wells coated with NMGB (A) or Naid60 (B) in a dose-dependent manner. scFv of Naid60 also inhibited the complement-mediated bactericidal activity of HmenB3 against NMGB in a dose-dependent manner (C). E. coli expressing scFv recombinant antibody was induced by IPTG and the expected scFv product of 30 kDa could be found by immunoblotting using HmenB3 (D).
Figure 7A:
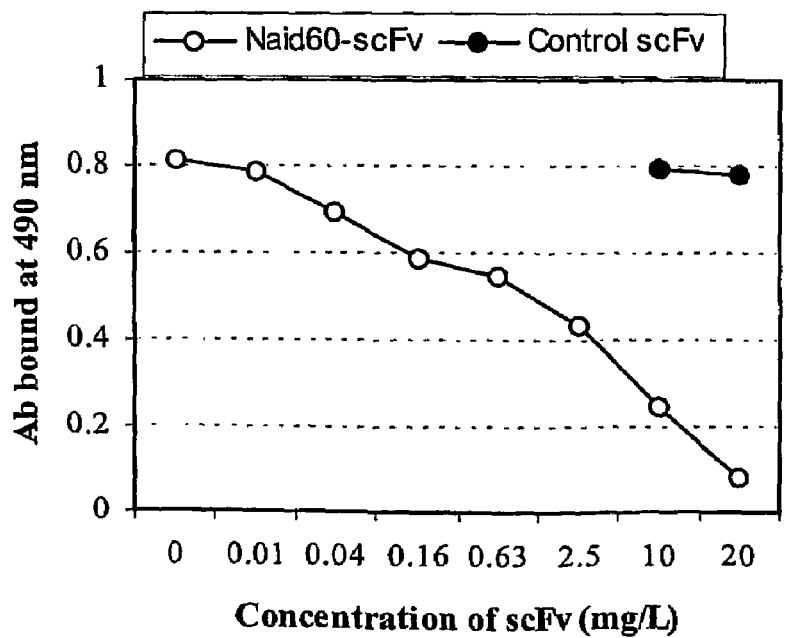

The phages displaying scFv of Naid60 on their surfaces were selected by one round of panning on EIA plagte coated with HmenB3 (100 μg/mL) in carbonate buffer (pH 9.6). The amplified phages giving a positive ELISA signal were then used to produce soluble scFv antibodies. For the production of soluble scFv antibodies, the scFv gene was cloned into the pRSET Sfi I/Not I expression vector, which was then used to transform *E. coli* BL21(DE3). The expression of scFv antibodies was confirmed by Western blot analysis. Naid60-scFv antibodies showed single monomer band at the expected molecular weight of 30 kDa (FIG. 7D).

Figure 7B:
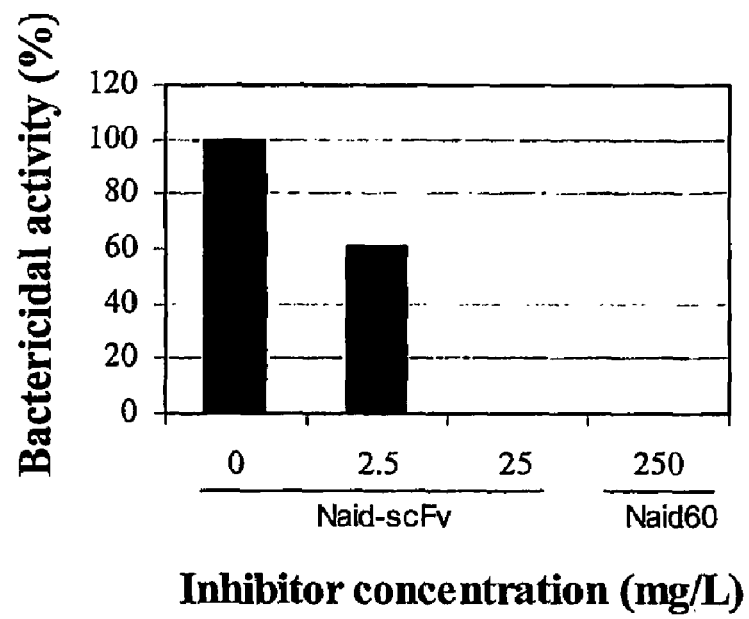
Figure 7B:
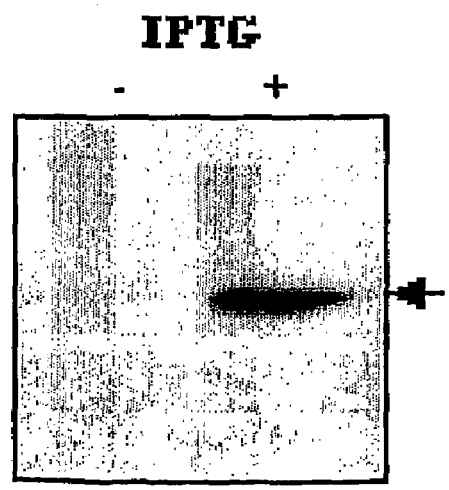

Affinity-purified scFv antibodies inhibited the binding of HmenB3 to NMGB (FIG. 7A) and to Naid60 (FIG. 7B) in a dose-dependent manner by ELISA assay. In addition, the bactericidal activity of HmenB3 against NMGB was inhibited in the presence of Naid60-scFv antibodies (FIG. 7C), suggesting that Naid60-scFv has a peptide mimicry epitope to NMGB PS, and can be used as an alternative immunogen to Naid60.

Example 6

Bactericidal Activity of Anti-Naid60 MAb (2-7-34)

Figure 8A:
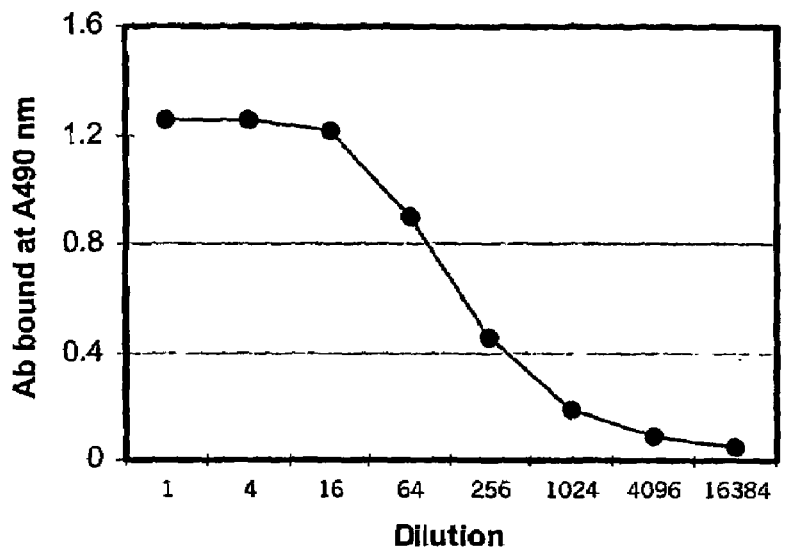
FIG. 8 depicts the bactericidal activity of 2-7-34 antibody, anti-Naid60 Ab, to NMGB. (A) Binding of 2-7-34 to the wells coated with NMGB. The binding of 2-7-34 to NMGB was decreased as the dilutions of antibody were increased. (B) 2-7-34 has complement-mediated bactericidal activity against NMGB. (C) depicts the inhibition of bactericidal activity of 2-7-34 to NMGB in the presence of Naid60. These data show that Naid60 has a peptide mimicry site to the NMGB PS to elicit bactericidal antibody.
Figure 8A:
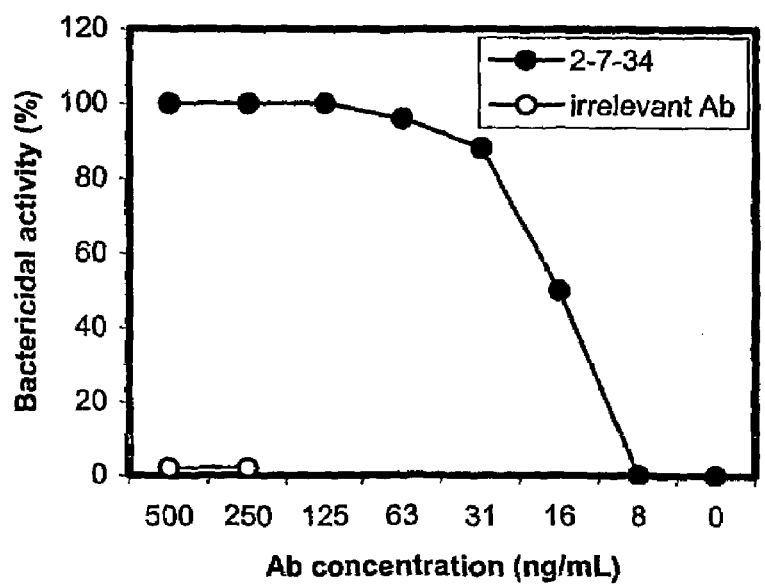
Figure 8B:
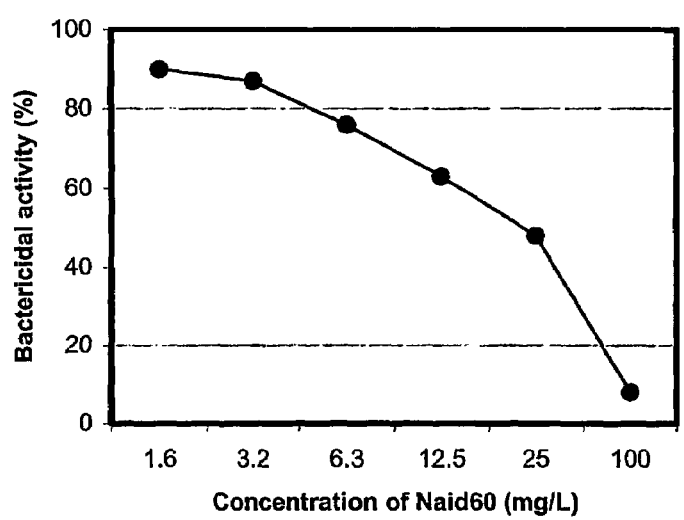
Figure 9:
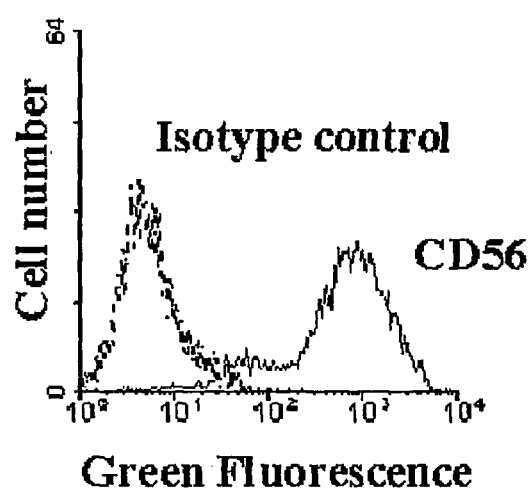
FIG. 9 depicts the autoreactivity of 2-7-34. (A) The number of CHP-134 cells (y axis) versus cellular fluorescence (x axis) were shown by flow cytometry. (Left) CHP-134 cells were stained with anti-CD56 or irrelevant isotype control antibody. (Right) Cells were stained with 100 μg/mL of 2-7-34 or 10 μg/mL of HmenB1 or isotype control antibody (dotted line). (B) A cryosection of 1- or 2-week-old mouse brain (cerebellum) was stained with A: 50 μg/mL 2-7-34, B: 50 μg/mL of irrelevant antibody, C: 0.1 μg/mL of HmenB1, and D: Hematoxyline/Eosin. Positive-staining cells have a brick-red color.
Figure 9:
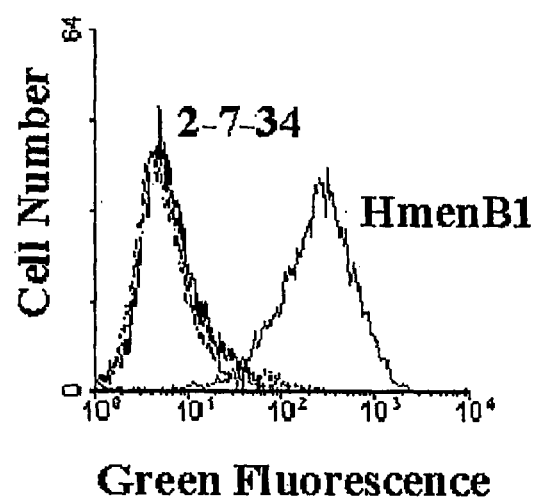
Figure 9:
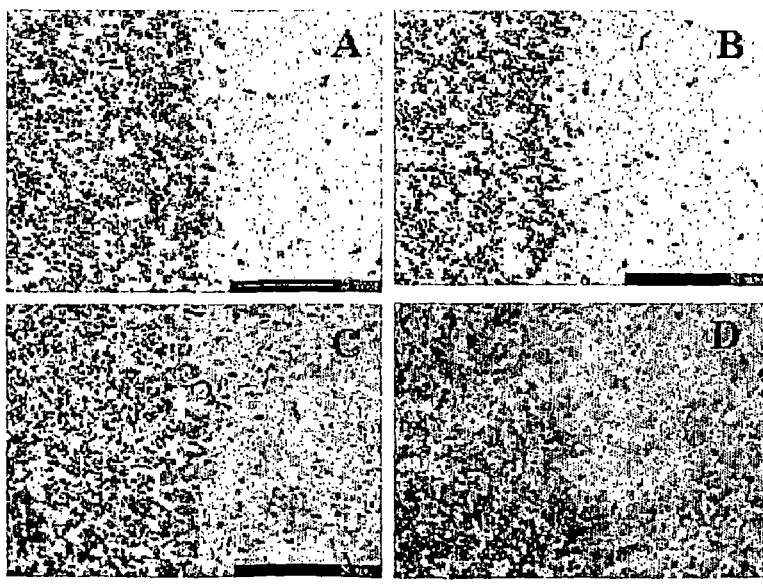

To test whether Naid60 has the epitope of NMGB and elicits antibody to kill NMGB, an anti-anti-idiotypic MAb (Ab3) was produced from mice immunized with Naid60 and named "2-7-34". 2-7-34 was screened by binding to Naid60 (Ab2), and also bound to the NMGB-coated wells in a dose-dependent manner by ELISA (FIG. 8A). 2-7-34 has bactericidal activity to kill NMGB strain ATCC No. 13090 dose-dependently in the presence of rabbit complement, with an $LD_{50}$ of 8 ng/mL (FIG. 8B). The killing could be observed in NMGB strain H44/76 (data not shown). And the bactericidal activity of 2-7-34 to NMGB was inhibited by Naid60 (FIG. 8C), demonstrating that Naid60 mimics NMGB PS to elicit antibodies to bind and kill NMGB.

Example 7

Autoimmunity Test of Anti-Naid60 Antibody (2-7-34)

One of the important issues in the development of a vaccine of NMGB is autoimmunity. Cross-reactivity of 2-7-34 with polysialic acid was initially assessed with a human neuroblastoma cell line, CHP-134. HmenB1 had moderate or strong binding to CHP-134 cells at approximately 10 µg/mL (FIG. 9A) (Shin, J. S., et al., Infect Immun 69, 3335-3342 (2001)). However, 2-7-34 did not detectably bind to CHP-134 cells detectably even at a high concentration of 100 µg/mL.

To further delineate the binding of 2-7-34 to brain tissue, we examined 2-7-34 for binding to the frozen section of the brain of a newborn mouse. HmenB1 stained scattered cells in the cerebrum and the Purkinje cells of the cerebellum at a low concentration of 0.1 µg/mL (C of FIG. 9B). In contrast, 2-7-34 did not stain the brain at a concentration of 50 µg/mL (A of FIG. 9B) and even at a high concentration of 100 g/mL (data not shown) as like the isotype-matched irrelevant mouse MAb. This finding supports the conclusion that 2-7-34 is not reactive with polysialic acid produced by animal tissues and that Naid60 has peptide mimicry epitope to NMGB PS, which is not cross-reactive with polysialic acid.

APPLICABILITY OF THIS INVENTION

*N. meningitidis* serogroup B vaccine is not available because the NMGB PS is poorly immunogenic and may elicit autoantibodies to neuronal tissue. The present invention provides an anti-idiotypic monoclonal antibody of Naid60, which mimics NMGB PS. This mimic peptide in monoclonal antibody can elicit antibodies to bind and kill NMGB, and which show no binding to neuronal tissue. The compositions using the Naid60 or its derivatives including pharmaceutically acceptable excipient can be used for effective prevention and treatment of group B meningococcal disease.

What is claimed is:

1. An anti-idiotypic monoclonal antibody or fragment thereof, wherein the anti-idiotypic antibody or fragment thereof:

(a) elicits antibodies against *Neisseria meningitidis* serogroup B; and (b) comprises the amino acid sequences of SEQ ID NO:5 for the heavy chains of the variable regions and of SEQ ID NO:6 for the light chains of the variable regions.

2. An immunogenic composition comprising the anti-idiotypic monoclonal antibody or fragment thereof of claim 1, and pharmaceutically acceptable excipients.

* * * * *

SEQUENCE LISTING

<160> NUMBER OF SEQ ID NOS: 14

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
cagcttgatt ttccttgtcc tta 23

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
gtgcacaccg ctggacaggg atcc 24

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
gacattcagc tgacccagtc tcca 24

<210> SEQ ID NO 4
<211> LENGTH: 14
<212> TYPE: DNA
<213> ORGANISM: Artificial Sequence
<220> FEATURE:
<223> OTHER INFORMATION: primer

<400> SEQUENCE: 4
tggtgggaag atgg 14

<210> SEQ ID NO 5

```
<211> LENGTH: 116
<212> TYPE: PRT
<213> ORGANISM: Artificial Sequence
<220> FEATURE:
<223> OTHER INFORMATION: amino acid sequences of Naid60 VH

<400> SEQUENCE: 5
```

| | | | | | | | | | | | | | | | |
|---|---|---|---|---|---|---|---|---|---|---|---|---|---|---|---|
| Glu | Val | Lys | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Lys | Leu | Ser | Cys | Ala | Thr | Ser | Gly | Phe | Leu | Phe | Thr | Asp | Tyr |
| | | | 20 | | | | | 25 | | | | | 30 | | |
| Tyr | Met | Phe | Trp | Val | Arg | Gln | Thr | Pro | Glu | Lys | Arg | Leu | Glu | Trp | Val |
| | | 35 | | | | | 40 | | | | | 45 | | | |
| Ala | Tyr | Ile | Ser | Asn | Gly | Gly | Gly | Asp | Thr | Tyr | Tyr | Pro | Asp | Thr | Val |
| | 50 | | | | | 55 | | | | | 60 | | | | |
| Lys | Gly | Arg | Phe | Thr | Ile | Ser | Arg | Asp | Asn | Ala | Lys | Asn | Ala | Leu | Tyr |
| 65 | | | | | 70 | | | | | 75 | | | | | 80 |
| Leu | Gln | Met | Ser | Arg | Leu | Lys | Ser | Glu | Asp | Thr | Ala | Met | Tyr | Tyr | Cys |
| | | | | 85 | | | | | 90 | | | | | 95 | |
| Ala | Arg | His | Lys | Gly | Tyr | Tyr | Gly | Tyr | Tyr | Tyr | Ala | Leu | Asp | Tyr | Trp |
| | | | 100 | | | | | 105 | | | | | 110 | | |
| Gly | Gln | Gly | Thr | | | | | | | | | | | | |
| | | | 115 | | | | | | | | | | | | |

```
<210> SEQ ID NO 6
<211> LENGTH: 103
<212> TYPE: PRT
<213> ORGANISM: Artificial Sequence
<220> FEATURE:
<223> OTHER INFORMATION: amino acid sequences of Naid60 VL

<400> SEQUENCE: 6
```

| | | | | | | | | | | | | | | | |
|---|---|---|---|---|---|---|---|---|---|---|---|---|---|---|---|
| Asp | Ile | Gln | Leu | Thr | Gln | Ser | Pro | Ala | Thr | Leu | Ser | Val | Thr | Pro | Gly |
| 1 | | | | 5 | | | | | 10 | | | | | 15 | |
| Asp | Ser | Val | Ser | Leu | Ser | Cys | Arg | Ala | Ser | Gln | Ser | Ile | Ser | Asn | Asn |
| | | | 20 | | | | | 25 | | | | | 30 | | |
| Leu | His | Trp | Tyr | Gln | Gln | Lys | Ser | His | Glu | Ser | Pro | Arg | Leu | Leu | Ile |
| | | | | 35 | | | | | 40 | | | | | 45 | |
| Lys | Tyr | Ala | Ser | Gln | Ser | Ile | Ser | Gly | Ile | Pro | Ser | Arg | Phe | Ser | Gly |
| | 50 | | | | | 55 | | | | | 60 | | | | |
| Ser | Gly | Ser | Gly | Thr | Asp | Phe | Thr | Leu | Ser | Ile | Asn | Ser | Val | Glu | Thr |
| 65 | | | | | 70 | | | | | 75 | | | | | 80 |
| Glu | Asp | Phe | Gly | Met | Tyr | Phe | Cys | Gln | Gln | Ser | Asn | Asn | Trp | Pro | Leu |
| | | | | 85 | | | | | 90 | | | | | 95 | |
| Thr | Phe | Gly | Ala | Gly | Thr | Lys | | | | | | | | | |
| | | | 100 | | | | | | | | | | | | |

```
<210> SEQ ID NO 7
<211> LENGTH: 348
<212> TYPE: DNA
<213> ORGANISM: Artificial Sequence
<220> FEATURE:
<223> OTHER INFORMATION: nucleotide sequence of Naid60 VH

<400> SEQUENCE: 7
gaagtgaagt tggtggagtc tgggggaggc ttagtgcagc ctggagggtc cctgaaactc      60
tcctgtgcaa cctctggatt ccttttcact gactattaca tgttttgggt tcgccagact     120
ccagagaaga ggctggagtg ggtcgcatac attagtaatg gtggtggtga cacctattat     180
```

```
ccagacactg taaagggccg attcaccatc tccagagaca atgccaagaa cgccctgtac      240
ctgcaaatga gccgtctgaa gtctgaggac acagccatgt attactgtgc aagacataag      300
ggctactatg gatattacta tgctttggac tactggggtc aaggaacc                   348
```

```
<210> SEQ ID NO 8
<211> LENGTH: 309
<212> TYPE: DNA
<213> ORGANISM: Artificial Sequence
<220> FEATURE:
<223> OTHER INFORMATION: nucleotide sequence of Naid60 VL

<400> SEQUENCE: 8
```

```
gacattcagc tgacccagtc tccagccacc ctgtctgtga ctccaggaga tagcgtcagt       60
ctttcctgca gggccagcca agtattagc aacaacctac actggtatca acaaaaatca      120
catgagtctc caaggcttct catcaagtat gcttcccagt ccatctctgg gatcccctcc     180
aggttcagtg gcagtggatc aggacagat ttcactctca gtatcaacag tgtggagact      240
gaagattttg gaatgtattt ctgtcaacag agtaacaact ggcctctcac gttcggtgct      300
gggaccaag                                                              309
```

```
<210> SEQ ID NO 9
<211> LENGTH: 15
<212> TYPE: PRT
<213> ORGANISM: Artificial Sequence
<220> FEATURE:
<223> OTHER INFORMATION: pNaid60 peptide

<400> SEQUENCE: 9

Cys Ala Arg His Lys Gly Tyr Tyr Gly Tyr Tyr Tyr Ala Leu Asp
1               5                   10                  15
```

```
<210> SEQ ID NO 10
<211> LENGTH: 12
<212> TYPE: PRT
<213> ORGANISM: Artificial Sequence
<220> FEATURE:
<223> OTHER INFORMATION: peptide sequence of CDR1

<400> SEQUENCE: 10

Cys Ala Thr Ser Gly Phe Leu Phe Thr Asp Tyr Tyr
1               5                   10
```

```
<210> SEQ ID NO 11
<211> LENGTH: 12
<212> TYPE: PRT
<213> ORGANISM: Artificial Sequence
<220> FEATURE:
<223> OTHER INFORMATION: peptide sequence of CDR2

<400> SEQUENCE: 11

Val Ala Tyr Ile Ser Asn Gly Gly Gly Asp Thr Tyr
1               5                   10
```

```
<210> SEQ ID NO 12
<211> LENGTH: 12
<212> TYPE: PRT
<213> ORGANISM: Artificial Sequence
<220> FEATURE:
<223> OTHER INFORMATION: peptide sequence of CDR1

<400> SEQUENCE: 12

Cys Arg Ala Ser Gln Ser Ile Ser Asn Asn Leu His
1               5                   10
```

-continued

```
<210> SEQ ID NO 13
<211> LENGTH: 14
<212> TYPE: PRT
<213> ORGANISM: Artificial Sequence
<220> FEATURE:
<223> OTHER INFORMATION: peptide sequence of CDR2

<400> SEQUENCE: 13

Leu Ile Lys Tyr Ala Ser Gln Ser Ile Ser Gly Ile Pro Ser
1               5                   10

<210> SEQ ID NO 14
<211> LENGTH: 14
<212> TYPE: PRT
<213> ORGANISM: Artificial Sequence
<220> FEATURE:
<223> OTHER INFORMATION: peptide sequence of CDR3

<400> SEQUENCE: 14

Tyr Phe Cys Gln Gln Ser Asn Asn Trp Pro Leu Thr Phe Gly
1               5                   10
```